US009176251B2

(12) United States Patent
Singer et al.

(10) Patent No.: US 9,176,251 B2
(45) Date of Patent: Nov. 3, 2015

(54) ASPHALTENE EVALUATION BASED ON NMR MEASUREMENTS AND TEMPERATURE / PRESSURE CYCLING

(71) Applicant: SCHLUMBERGER TECHNOLOGY CORPORATION, Sugar Land, TX (US)

(72) Inventors: Philip M. Singer, Richmond, TX (US); Patrice Ligneul, Chaville (FR); Edward Alan Clerke, Dhahran (SA); Johannes J. M. Buiting, Didam (NL)

(73) Assignees: Schlumberger Technology Corporation, Sugar Land, TX (US); Saudi Arabian Oil Company (SA)

(*) Notice: Subject to any disclaimer, the term of this patent is extended or adjusted under 35 U.S.C. 154(b) by 552 days.

(21) Appl. No.: 13/673,772

(22) Filed: Nov. 9, 2012

(65) Prior Publication Data
US 2014/0132258 A1  May 15, 2014

(51) Int. Cl.
G01V 3/00 (2006.01)
G01V 3/32 (2006.01)
E21B 49/00 (2006.01)
G01V 3/14 (2006.01)
G01N 33/24 (2006.01)

(52) U.S. Cl.
CPC . G01V 3/32 (2013.01); E21B 49/00 (2013.01); G01N 33/241 (2013.01); G01V 3/14 (2013.01)

(58) Field of Classification Search
CPC .......................................................... G01V 3/32
USPC .......................................................... 324/303
See application file for complete search history.

(56) References Cited

U.S. PATENT DOCUMENTS 6,883,702 B2    4/2005  Hurlimann et al.
2005/0242807 A1 11/2005  Freedman
2007/0134804 A1* 6/2007  Fisher et al. .................. 436/164
2009/0091320 A1 4/2009  Flaum et al.
(Continued)

FOREIGN PATENT DOCUMENTS

WO    2011091269 A2    7/2011

OTHER PUBLICATIONS

Akbarzadeh, et al., "Asphaltenes—Problematic but Rich in Potential", Oil Field Review, Summer 2007, pp. 22-43.
(Continued)

Primary Examiner — Rodney Fuller
(74) Attorney, Agent, or Firm — Bridget M. Laffey; Jakub Michna; Daniel S. Matthews

(57) ABSTRACT

Asphaltene content and its spatial distribution in a reservoir containing crude oil is an important factor in determining the potential for formation damage and pipeline impairment, as well as planning for processing and refining of the oil. Exemplary uses include: reservoir modeling, development and depletion planning, pressure maintenance, and surface facilities management. A convenient method has been developed which uses two-dimensional NMR techniques during a temperature and/or pressure cycle to quantify the asphaltene content of the crude oil without the need for extracting the oil from the reservoir rock. The technique can be applied to core, down-hole logs, or, a combination of both.

23 Claims, 8 Drawing Sheets

(56) References Cited

U.S. PATENT DOCUMENTS

| | | |
|---|---|---|
| 2009/0288881 A1 | 11/2009 | Mullins et al. |
| 2011/0088895 A1* | 4/2011 | Pop et al. .................... 166/254.2 |
| 2011/0162558 A1* | 7/2011 | Mena Cervantes et al. .. 106/506 |
| 2013/0112406 A1* | 5/2013 | Zuo et al. .................. 166/250.08 |
| 2014/0238670 A1* | 8/2014 | Pop et al. ....................... 166/264 |
| 2014/0253116 A1* | 9/2014 | Freedman et al. ............. 324/303 |
| 2014/0327552 A1* | 11/2014 | Filas et al. ................. 340/854.6 |

OTHER PUBLICATIONS

Mutina, et al., "Correlation of Transverse and Rotational Diffusion Coefficient: A Probe of Chemical Composition in Hydrocarbon Oils", Journal of Physical Chemistry A, vol. 112(15), 2008, pp. 3291-3301.

International Search Report and Written Opinion issued in PCT/US2013/066723 on Feb. 6, 2014, 10 pages.

\* cited by examiner

ASPHALTENE EVALUATION BASED ON NMR MEASUREMENTS AND TEMPERATURE / PRESSURE CYCLING

BACKGROUND

Asphaltene content is an important factor in determining crude oil physical properties for subsurface reservoir modeling and for the processing and refining paths of a crude oil. A known laboratory technique known as SARA (saturates, aromatics, resins and asphaltenes) analysis is a relatively lengthy method for the determination of these subcomponent group volumes by mass within the multicomponent crude oil. A more convenient method to quantify asphaltene fraction rapidly and deployable in a downhole or surface configuration is desirable.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

According to some embodiments, a method of asphaltene evaluation of a hydrocarbon-bearing rock sample from a subterranean rock formation is described. The method includes: making a first NMR measurement representative of the hydrocarbon-bearing rock sample at temperature and pressure conditions prior to asphaltene precipitation onset; lowering temperature and/or pressure of the hydrocarbon-bearing rock sample below an expected asphaltene precipitation onset condition; subsequently raising the temperature and/or pressure conditions above the expected asphaltene precipitation onset condition; making a second NMR measurement on the hydrocarbon-bearing rock while at conditions above the expected asphaltene precipitation onset condition; and evaluating the asphaltene content of oil in the hydrocarbon-bearing rock sample based at least in part on a comparison of the first and second NMR measurements.

According to some embodiments, the first NMR measurement is made downhole using a downhole NMR tool while the rock sample is located in-situ within the subterranean rock formation, and according to alternative embodiments the first NMR measurement is made on the surface (or down-hole) on the rock sample while being preserved at reservoir temperature and pressure conditions. According to some embodiments, the temperature and pressure conditions of the rock sample for the first NMR measurement are substantially the same as temperature and pressure conditions of the rock sample for the second NMR measurement. The first and second NMR measurements are diffusion-relaxation NMR measurements, such as Diffusion-$T_1$ or Diffusion-$T_2$ measurements. The first NMR measurement is also made prior to production from the subterranean formation. The expected asphaltene precipitation onset condition is the critical point for asphaltene flocculation-dissolution on the asphaltene-precipitation envelope. According to some embodiments a mapping is made of the first and second measurements in Diffusion and Relaxation ($T_1$ or $T_2$) space, the 2D (2 dimensional) maps are evaluated for a shift in a fluid (maltene) tending to indicate significant presence of asphaltenes in the rock sample. The shift can indicate irreversible behavior of asphaltenes on wettability of pore surfaces within the rock sample.

According to some embodiments, a signal representing a water fluid is separated from a signal representing an oil fluid in data from the first and second NMR measurements, for example by using a diffusion-coefficient log-mean method or a manual method. A calibration can also be performed using laboratory analysis of saturates, aromatics, resins and asphaltenes conducted on extracted oil and NMR measurements on one or more other samples of rock with and without contained crude oil.

According to some embodiments, a system for asphaltene evaluation of a hydrocarbon-bearing rock sample from a subterranean rock formation is described. The system includes: a downhole NMR tool adapted to make a first NMR measurement of the subterranean rock formation at pressure conditions prior to asphaltene precipitation onset or at original reservoir temperature and pressure conditions; a facility for inducing and controlling a temperature and pressure change of a hydrocarbon-bearing rock sample, the facility being configured to lower the temperature and/or pressure of the sample to a point below an expected asphaltene precipitation onset condition, and subsequently raise the temperature and/or pressure conditions above the expected asphaltene precipitation onset condition or to return to original reservoir conditions and remake the downhole measurement looking for signal differences caused by the temperature or pressure cycling. According to some embodiments, the downhole measurements could be made on rock and crude oil volumes in the adjacent borehole wall or alternatively on downhole rock samples extracted from the formation wall using downhole rock sampling techniques. Alternatively, a surface NMR measurement facility adapted to make a second NMR measurement on the hydrocarbon-bearing rock sample while at conditions above the expected asphaltene precipitation onset condition, wherein an evaluation of asphaltene content in the hydrocarbon-bearing rock sample can be made based at least in part on a comparison of the first and second NMR measurements.

According to another embodiment, the system includes: a downhole NMR tool adapted to make a first NMR measurement of the subterranean rock formation at reservoir conditions whereby it is observed that the two dimensional oil and water signals are not resolved to the desired accuracy and precision. Hence, a facility for inducing and controlling a temperature and pressure change of the hydrocarbon and water bearing rock sample is utilized to change the measurement conditions (temperature or pressure) to improve the oil and water signal resolution in the two dimensional signal domain. Subsequently the sample is returned to original conditions and the resolved information obtained at the altered temperature or pressure is used as a constraint on the interpretation of the reservoir condition deconvolution of the oil and water two dimensional signals. According to some embodiments, the downhole measurements could be made on rock and crude oil volumes in the adjacent borehole wall or alternatively on downhole rock samples extracted from the formation wall using downhole rock sampling techniques. Alternatively, a surface NMR measurement facility adapted to make a second NMR measurement on the hydrocarbon-bearing rock sample while at reservoir conditions and altered condition which improves signal resolution and a means to return the sample to the original reservoir condition.

BRIEF DESCRIPTION OF THE DRAWINGS

The subject disclosure is further described in the detailed description which follows, in reference to the noted plurality of drawings by way of non-limiting examples of embodiments of the subject disclosure, in which like reference numerals represent similar parts throughout the several views of the drawings, and wherein.

DETAILED DESCRIPTION

Figure 1:
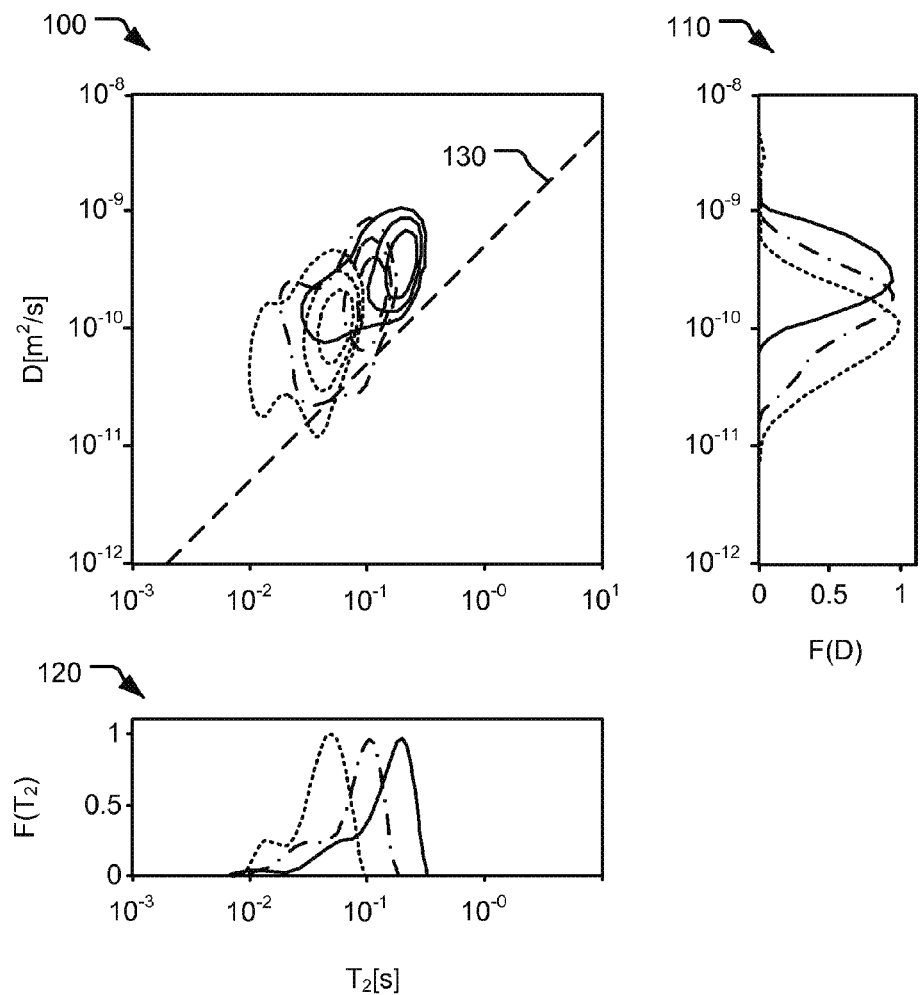
FIG. 1 shows Diffusion-$T_2$ distributions for a bulk crude oil with high Asphaltene content (about 4 wt %) as a function of temperature.

The particulars shown herein are by way of example and for purposes of illustrative discussion of the embodiments of the subject disclosure only and are presented in the cause of providing what is believed to be the most useful and readily understood description of the principles and conceptual aspects of the subject disclosure. In this regard, no attempt is made to show structural details of the subject disclosure in more detail than is necessary for the fundamental understanding of the subject disclosure, the description taken with the drawings making apparent to those skilled in the art how the several forms of the subject disclosure may be embodied in practice. Further, like reference numbers and designations in the various drawings indicate like elements.

Two-dimensional NMR signals composed of NMR decay time and diffusion time measurement are usually performed at the native borehole-formation temperatures. However, the separation of the signal components in this two-dimensional space into water and oil relaxation times and fluids that wet the rock surface with altered relaxation times is strongly affected by the temperature at which the measurement is performed. Varying the measurement temperature can separate or merge the signal in the diffusion time domain between the fluid components very strongly while the signal also experiences some weaker temperature related broadening or narrowing. These signals are typically measured at the formation temperature. For a more complete interpretation, these temperature effects can be modeled and compensated for, to compare to laboratory ambient conditions.

According to some embodiments, the temperature of the downhole measurement volume of interest containing reservoir fluids and rock can be altered by a heating or cooling device over a small volume of investigation and this temperature can be designed and selected to create maximum resolution of the separating and broadening NMR signals. In addition, according to some embodiments, local temperature reductions and increases can be used to close and narrow the signals and then widen and spread the signals as desired. Temperature scans and loops could also be programmed for various purposes so as to emphasize certain properties of the multicomponent hydrocarbon mixture which are irreversible in relation to multicomponent phase behavior of hydrocarbons containing asphaltenes, waxes and other subcomponents whose state and behavior would be modified by the temperature scans and loops.

According to some embodiments, asphaltene analysis is described which takes advantage of the fact that oil (and oil components) and water do not behave the same way at various temperatures. In particular, according to some embodiments a temperature ramp can be used (from very cold, say 10 C, to very high, say 150 C) to characterize the individual thermodynamic behaviour of fluids through their NMR response (which may include some rock mechanics inversions).

Reservoir oils can contain high asphaltene content, and asphaltene is known to have irreversible behaviour (hysteresis) when it comes to wettability on a rock surface. According to some embodiments NMR measurements are included in pressure and temperature cycling on preserved core, which pass across the critical point for asphaltene flocculation-dissolution. Findings can then be categorized into two broad classes: (1) if the NMR results are repeatable (reversible) during the pressure and temperature cycle, then no asphaltene effect can be detected and it is concluded that the oil saturating the core contains minimal asphaltene content; and (2) if the NMR results are irreversible during the pressure and temperature cycle, then asphaltenes have deposited and wetted the rock surface in an irreversible manner, and it is concluded that the oil saturating the core contains significant asphaltene content (>1 wt %). According to some embodiments, a quick in-situ estimate of asphaltene content in preserved cores using NMR is provided, which can be calibrated with SARA analysis from the oil extracted from the core.

Asphaltenes are known to have significant effects on the NMR response of bulk crude oils. For example FIG. 1 shows Diffusion-$T_2$ distributions for a bulk crude oil with high asphaltene content (about 4 wt %), measured at 10, 30 and 50° C., shown as dotted line, dashed-dotted line and solid line, respectively. Central plot 100 is the 2D map, while right panel 110 is the 1D projection of Diffusion, and the bottom panel 120 is the 1D projection of $T_2$. Dashed diagonal line 130 is the oil correlation line where Alkanes are known to reside. Data for FIG. 1 is from "Correlation of Transverse and Rotational Diffusion Coefficient: A Probe of Chemical Composition in Hydrocarbon Oils," Albina R. Mutina, Martin D. Hurlimann, J. Phys. Chem. A 2008, 112, 3291-3301.

The effect of increasing temperature is to decrease the oil viscosity ($\eta$), which results in an increase in both Diffusion ($\sim 1/\eta^\alpha$) and $T_2$ relaxation ($\sim 1/\eta^\alpha$), where the exponent $\alpha$ is known to be within the range $0 \Leftrightarrow 1$. Also, the majority of the signal in the 2D map lies to the left of the diagonal oil correlation line for Alkanes (known to be at $5 \times 10^{-10}$ m$^2$/s$^2$), which is an indication of high Asphaltene content throughout the temperature range (i.e., no dissolution). It can be seen that the Diffusion-$T_2$ relaxation map of a crude oil is both a good measure of oil viscosity and good indicator of asphaltene content, as a function of temperature.

Note that the 4 wt % of asphaltene is NMR invisible due its very short $T_2$ relaxation times. The NMR signal shown in FIG. 1 comprises the remaining 96 wt % of non-asphaltene components (maltenes) in the oil, which is heavily influenced by the presence of the 4 wt % of asphaltene in solution.

When asphaltenes drop out of solution in a crude oil, the main effect is to decrease the oil viscosity resulting in an increase in both Diffusion and $T_2$ of the remaining maltene. The secondary effect is to push the remaining pure maltene signal onto the diagonal oil correlation line for alkanes.

In cases where crude oil is saturating a porous rock, an additional effect comes into play when the asphaltenes come out of solution, flocculate and then coat the rock surface. In such cases, the maltene viscosity is lower and therefore the Diffusion and $T_2$ are larger, however, the asphaltenes on the pore surfaces create additional surface relaxation for the maltenes whenever they encounter the pore walls. This enhanced relaxation due to surface relaxivity shortens the $T_2$ relaxation time of the maltene, without significantly effecting the Diffusion. The net effect is to once again drive the maltene signal to the left of the oil correlation line for alkanes.

According to some embodiments, ramping and cycling of temperature and pressure in a controlled manner will shift the crude oil signal over a wide range of Diffusion and $T_2$ in the manner described above. The extent of the various shifts in the 2D space will depend on asphaltene content and history of the saturating oil. If the critical point is reached, where asphaltenes drop out and permanently coat the pore walls, the enhanced surface relaxation for the maltenes will be detected, and the Diffusion-$T_2$ coordinates before the critical point was reached will not re-occur. This would signal an irreversible (i.e., hysteretic) cycle, which we have found to be a signature of high Asphaltene content (>1 wt %) in the crude oil.

Figure 2:
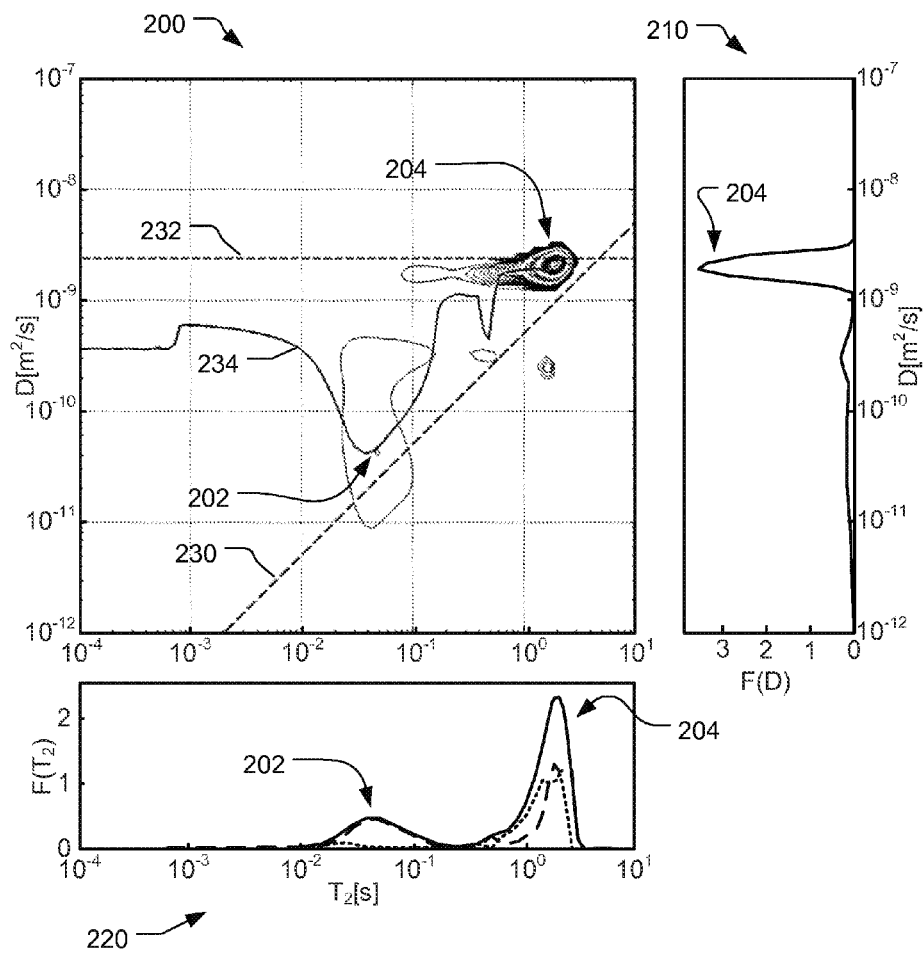
FIG. 2 shows a Diffusion-$T_2$ map for a carbonate rock in its preserved (i.e., Native) state at ambient temperature and pressure, according to some embodiments.

FIG. 2 shows a Diffusion-$T_2$ map for a carbonate rock in its preserved (i.e., Native) state, according to some embodiments. Diffusion-$T_2$ distribution 2D map 200 is for a native state core-plug saturated with oil and water, at ambient temperature (25° C.). The dashed horizontal line 232 is the water line, while the dashed diagonal line 230 is the oil correlation line for alkanes. The solid line 234 in the 2D map 200 is the DCLM (Diffusion Coefficient Log-Mean) of the distribution, which is used to separate the oil and water components in the $T_2$ projections shown in panel 220. Specifically, in panel 220 the oil is shown in dashed line, the water in dotted line, and the total in solid line.

In the example shown in FIG. 2, the rock is partially saturated with brine and crude oil. The saturating crude oil is known to have an asphaltene concentration of about 4 wt % according to SARA analysis, which is very similar to the bulk crude oil example shown in FIG. 1. The data in FIG. 2 is taken at ambient temperature (25° C.). The analysis of the 2D map 200 suggests that the signal 202 with short $T_2 \sim 4 \times 10^{-2}$ seconds is mostly oil, while the signal 204 at around $T_2 \sim 2 \times 10^0$ seconds is a mixture of both oil and water signals. Note that the separation of oil and water signals at $T_2 \sim 2 \times 10^0$ seconds is inaccurate since at this temperature the water and oil correlation lines 232 and 230 intersect at the range of interest.

Figure 3:
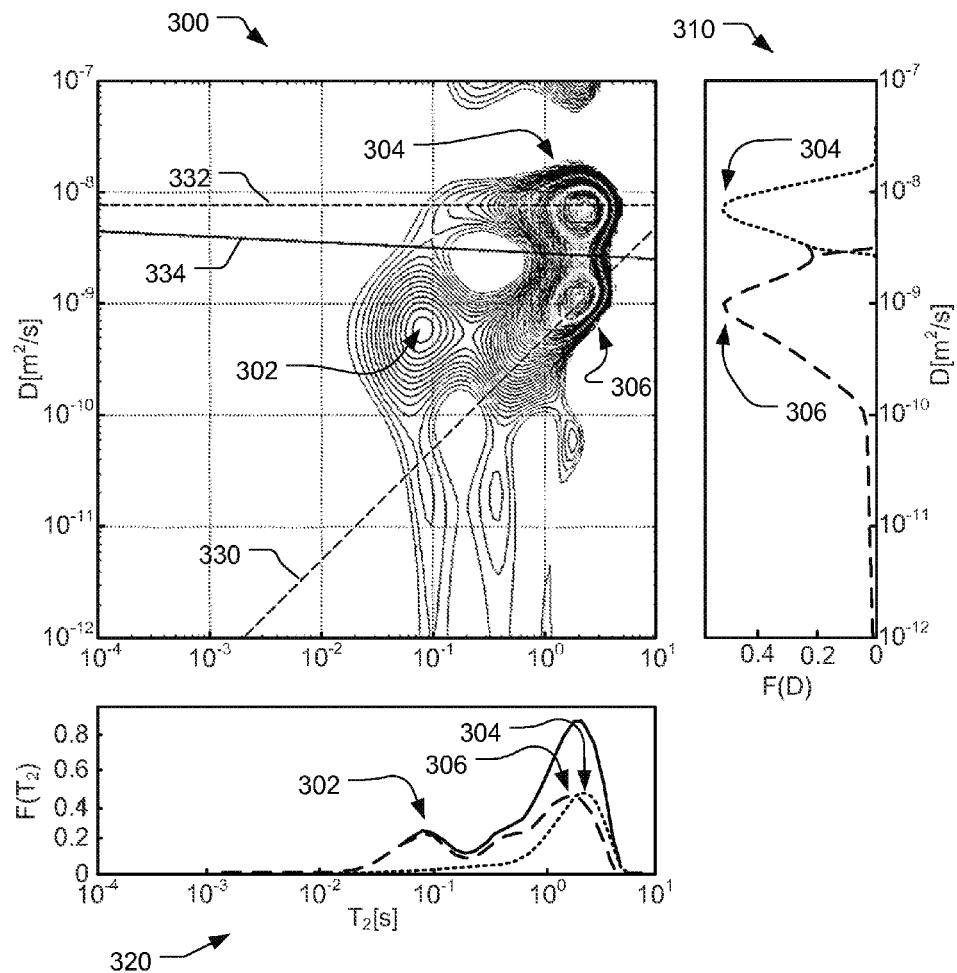
FIG. 3 shows a Diffusion-$T_2$ distribution for the same native-state core-plug as in FIG. 2, but measured at an elevated temperature of 100° C., according to some embodiments.

FIG. 3 shows a Diffusion-$T_2$ distribution for the same native-state core-plug as in FIG. 2, but measured at an elevated temperature of 100° C., according to some embodiments. The solid line 334 in the 2D map 300 indicates a manual separation of the distribution into the oil and water shown in the $T_2$ projections 310 and 320. In the 1D Diffusion projection panel 310, and the 1D $T_2$ projection panel 320, oil is shown in dashed line, water in dotted line, and the total in solid line. The signal 302 with short $T_2 \sim 8 \times 10^{-2}$ seconds is again (consistently) mostly oil, while the signal at long $T_2 \sim 2 \times 10$ seconds is now clearly separated into oil peak 306 and water peak 304.

It is evident from FIG. 3 that the native state plug is mixed wet. This can be deduced by separating the 3 fluid peaks 302, 304 and 306 as such: (1) partially wetting water with long $T_2 \sim 2 \times 10$ seconds (peak 304) lying primarily on the (unrestricted) water correlation line 332; (2) non-wetting oil with long $T_2 \sim 2 \times 10$ seconds (peak 306) lying primarily on the diagonal oil correlation line 330 for alkanes, indicating that the oil is a maltene; and (3) wetting oil with short $T_2 \sim 8 \times 10^{-2}$ seconds (peak 302) lying to the left of the diagonal oil correlation line 330, indicating that the maltene is in contact with pore surfaces coated with asphaltene.

Figure 5:
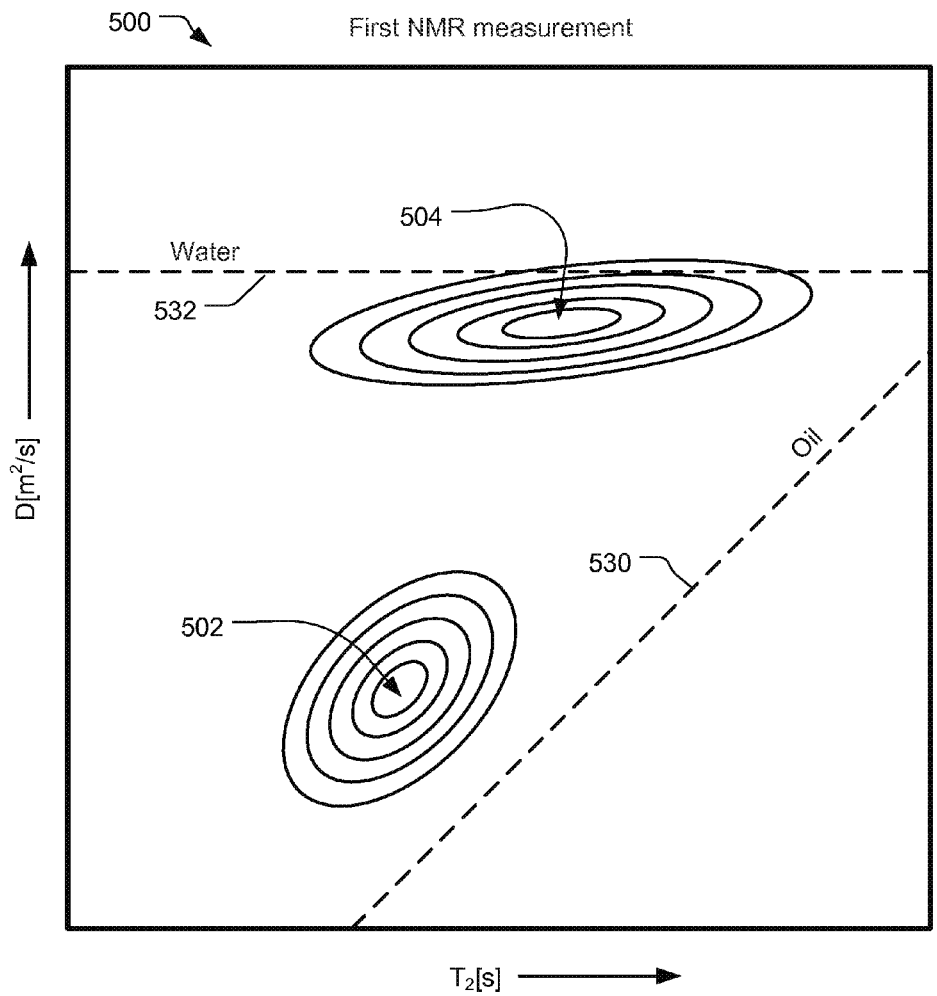
FIGS. 5-6 are diagrams illustrating simulated 2D Diffusion-$T_2$ distributions for a reservoir core sample, according to some embodiments.
Figure 6:
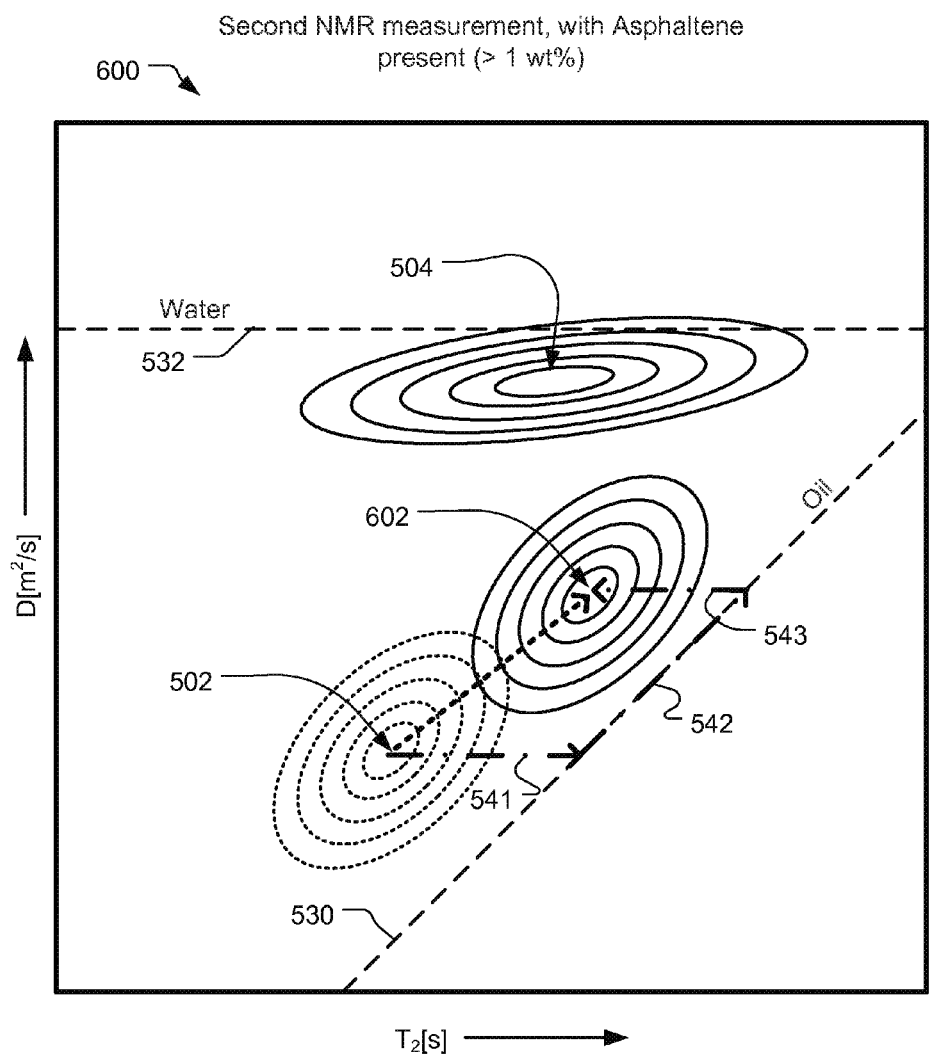

The first conclusion from the example of FIGS. 2 and 3 is that measurements at elevated reservoir conditions (FIG. 3) results in clearer separation of oil and water signals compared with measurements at ambient conditions (FIG. 2). The second conclusion is that this carbonate rock is mixed wet as a result of asphaltene drop out, flocculation and coating of some (but not all) of the pore walls. In other words, there is a significant concentration of asphaltene in this crude oil, which agrees with the independent SARA analysis on the extracted oil. According to some embodiments, a conclusion of significant concentration of asphaltene in the crude oil is based on a comparison of the NMR measurements of the saturated core at elevated temperature and pressure, as shown in FIG. 3, with NMR measurements made on the formation downhole while at the original reservoir conditions. This first NMR measurement (not shown) can be for example, made with a downhole NMR tool prior to extraction of the core sample. In the comparison between the NMR measurements before and after the temperature cycling, the conclusion of significant asphaltene concentrations depends on the observation of a shift in the signal of a fluid (maltene) which tends to indicate significant presence of asphaltenes in the rock sample. The observed signal shift indicates irreversible behavior of asphaltenes on wettability of pores surfaced within the rock sample. This shift is illustrated in FIGS. 5-6 below. According to some embodiments, other types of NMR 2D maps are used instead of Diffusion-$T_2$ maps as shown in FIGS. 2-3. For example, according to some embodiments Diffusion-$T_1$ or $T_1$-$T_2$ two-dimensional maps are used.

Figure 4:
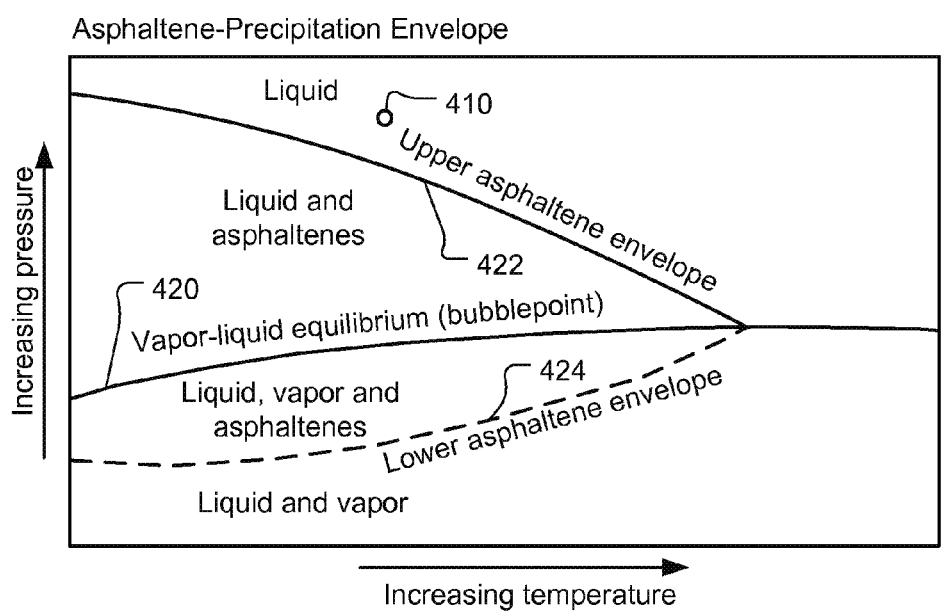
FIG. 4 is a diagram of an asphaltene-precipitation envelope (APE) in pressure-temperature space.

FIG. 4 is a diagram of an asphaltene-precipitation envelope (APE) in a pressure-temperature space. The asphaltene-precipitation envelope 422 and 424 delimits the stability zones for asphaltenes in solution. For given example reservoir conditions 410, primary depletion causes pressure to decrease. When pressure reaches the upper asphaltene-precipitation envelope 422, also known as the asphaltene-precipitation onset pressure, the least-soluble asphaltenes will precipitate. As pressure continues to decrease, more asphaltenes will precipitate, until the bubble-point pressure 420 is reached, and gas is released from solution. With continued pressure decrease, enough gas has been removed from the system, and the crude oil may begin to re-dissolve asphaltenes at the lower asphaltene-precipitation envelope 424. For further information on asphaltenes, see: K. Akbarzadeh et al., "Asphaltenes—Problematic but Rich in Potential," Oilfield Review, (2007).

FIGS. 5-6 are diagrams illustrating simulated 2D Diffusion-$T_2$ distributions for a reservoir core sample, according to some embodiments. The 2D map 500 shows a first set of NMR measurements taken of a core sample rock at the original reservoir pressure and temperature prior to passing through the asphaltene precipitation onset point. This could be for example from downhole NMR measurements of the reservoir rock prior to cutting of the core sample, or, a core sampled with a down-hole coring tool with in situ NMR capabilities. A signal 504 is shown near the water line 532 which corresponds to water. A signal 502 is to the left of oil correlation line 530. Without further information, the signal 502 could indicate: (1) non-wetting oil containing asphaltene; (2) wetting oil containing no asphaltene; or (3) a combination of the two.

In FIG. 6, 2D map 600 shows a second set of NMR measurements, following a cycling of temperature. The core sample temperature has been lowered to below the asphaltene precipitation onset point and then raised back up above the onset point. The 2D map 600 shows that the location of the signal peak has shifted from where it was prior to the cycling at location 502, to a location 602. The shift is shown by the dotted arrow. The dashed-dotted arrows 541, 542 and 543 show a breakdown of the shift which can be explained as follows. Asphaltene dropping out from oil results in an increase in maltene relaxation time, shown by arrow 541. Maltene viscosity ($\eta$) is lowered after the asphaltene drop out which causes an increase in maltene relaxation time ($\sim 1/\eta^\alpha$) as well as maltene Diffusion coefficient ($\sim 1/\eta^\alpha$), as shown by arrow 542. The exponent $\alpha$ is typically within the range $0 \Leftrightarrow 1$. Finally, asphaltene deposits on pore walls and the pores become oil wet which causes a decrease in Maltene relaxation time, as shown by arrow 543. The overall shift is seen by the new signal location 602 in map 600. From this shift, it can be determined that a significant amount (i.e., greater than 1% wt) of asphaltenes are present in the core sample. According to some embodiments, other types of NMR 2D maps are used instead of Diffusion-$T_2$ maps as shown in FIGS. 5-6. For example, according to some embodiments Diffusion-$T_1$ or $T_1$-$T_2$ two-dimensional maps are used.

In FIG. 6, the $T_2$ shift from asphaltene drop-out (541) is not necessarily the same magnitude as the $T_2$ shift from asphaltene deposit on pore walls (543). The consequence is that in the case (not shown here) where the exponent $\alpha \sim 0$ (defined above) results in a negligible shift (542) along the alkane line (530), a significant amount (i.e., greater than 1% wt) of asphaltene can be detected by the difference in magnitude of 541 and 543 along the $T_2$ axis alone.

Figure 7:
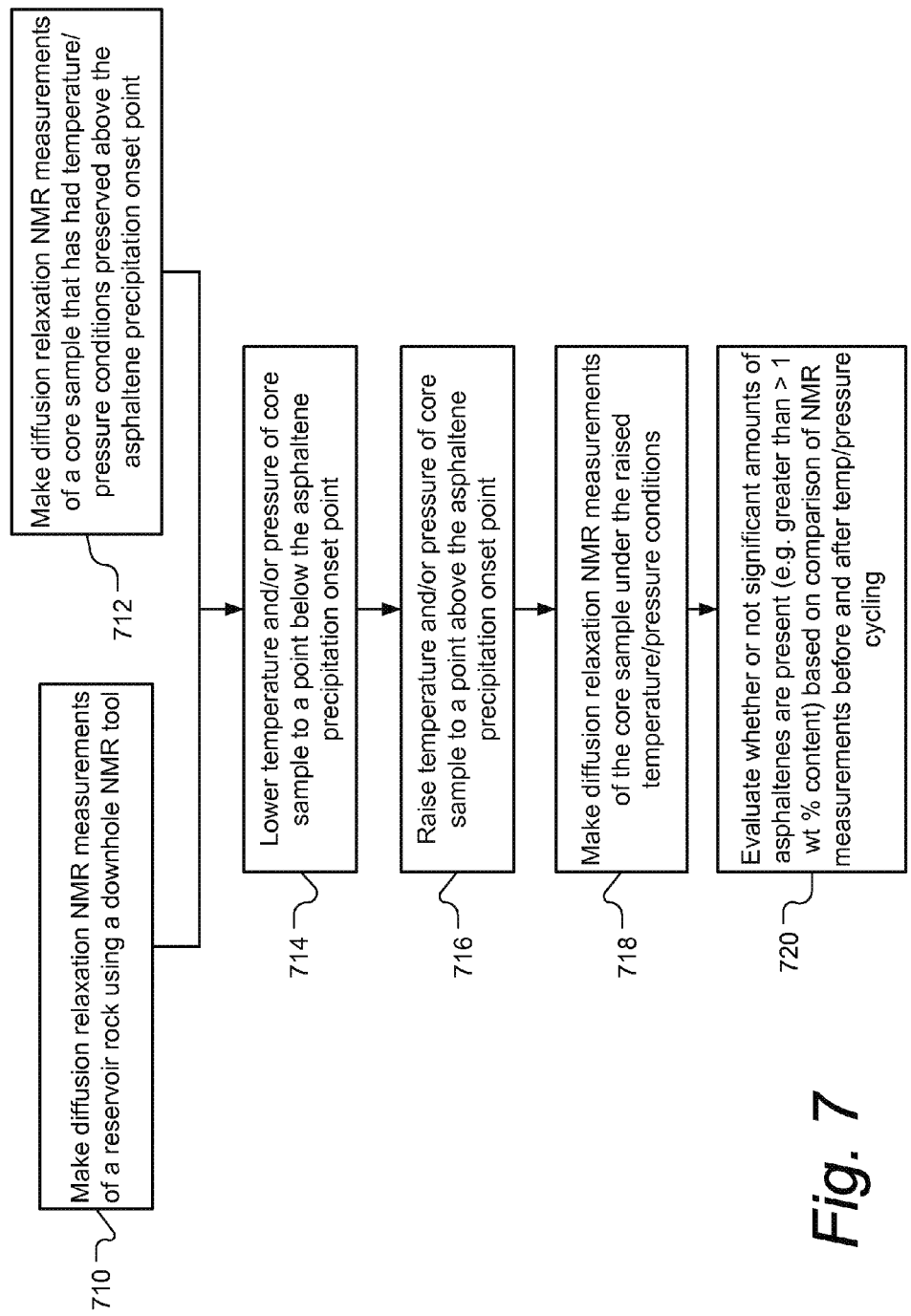
FIG. 7 is a flow chart illustrating aspects of a method for evaluating whether or not significant amounts of asphaltenes are present in a core sample, according to some embodiments.

FIG. 7 is a flow chart illustrating aspects of a method for evaluating whether or not significant amounts of asphaltenes are present in a core sample, according to some embodiments. In block 710, a first set of diffusion relaxation NMR measurements is taken of a reservoir rock in-situ downhole using a downhole NMR tool. According to an alternative embodiment, if the ability to preserve the temperature and pressure conditions of the core sample during transportation to the surface and to a laboratory facility exists, in block 712 the first set of NMR measurements can be made in a laboratory. For maximum accuracy and robustness, it is highly desirable that the first set of NMR measurements be made before the sample has first crossed the asphaltene precipitation onset point. Therefore, according to some embodiments, the first set of NMR measurements (in blocks 710 or 712) is made prior to significant lowering of pressure within the reservoir, which could happen for example during production draw down.

In block 714 the temperature and/or pressure of the core sample is lowered to a point below the asphaltene precipitation onset point. In block 715, the temperature and/or pressure are raised to a point back above the asphaltene precipitation onset point. According to some embodiments an effort is made to match the temperature and pressure conditions under which the first set of NMR measurements was taken. In block 718, a second set of diffusion relaxation NMR measurements is taken of the core sample while at the higher temperature/pressure conditions. In block 720, an evaluation is made whether or not significant amounts of asphaltenes are present (e.g., greater than >1 wt % content) based on a comparison of the first and second sets of NMR data (which can be mapped, for example such as shown in FIGS. 5 and 6 respectively).

According to some embodiments, various parameters are controlled for the asphaltene evaluation technique described herein. First, the temperature and pressure cycle of blocks 714 and 716 should be designed to cross the critical point for asphaltene drop out in a controlled manner. Second, the NMR data should be properly acquired before (as in blocks 710 or 712) and after (as in block 718) the irreversible process. Third, according to some embodiments, the technique for separating the different fluids in the 2D map is carefully chosen, for example, by either using the DCLM method as in FIG. 2, or by using a manual "by eye" method as in FIG. 3. It will be appreciated by those skilled in the art that the selection of such parameters and techniques will depend on the particular combination of reservoir rock and fluid under investigation, the reservoir conditions, and, the phase behaviour of the asphaltene in the crude oil. According to some embodiments a benchmarking or calibration of this technique, similar to the examples described herein, is carried out using a SARA analysis of the extracted oil from the core.

According to some embodiments, a down-hole tool can be provided that can core a rock sample, measure the first NMR, cycle the temperature and/or pressure to below and then back above the critical point, then measure second NMR, all while remaining down-hole. Alternatively, a downhole tool can be provided that can cool a portion of the rock in-situ to below the critical point for asphaltene drop out without cutting of a core sample, while the NMR tool measurements are made before and after the cooling. In both of these cases, blocks 712-718 would also be done completely downhole.

Figure 8:
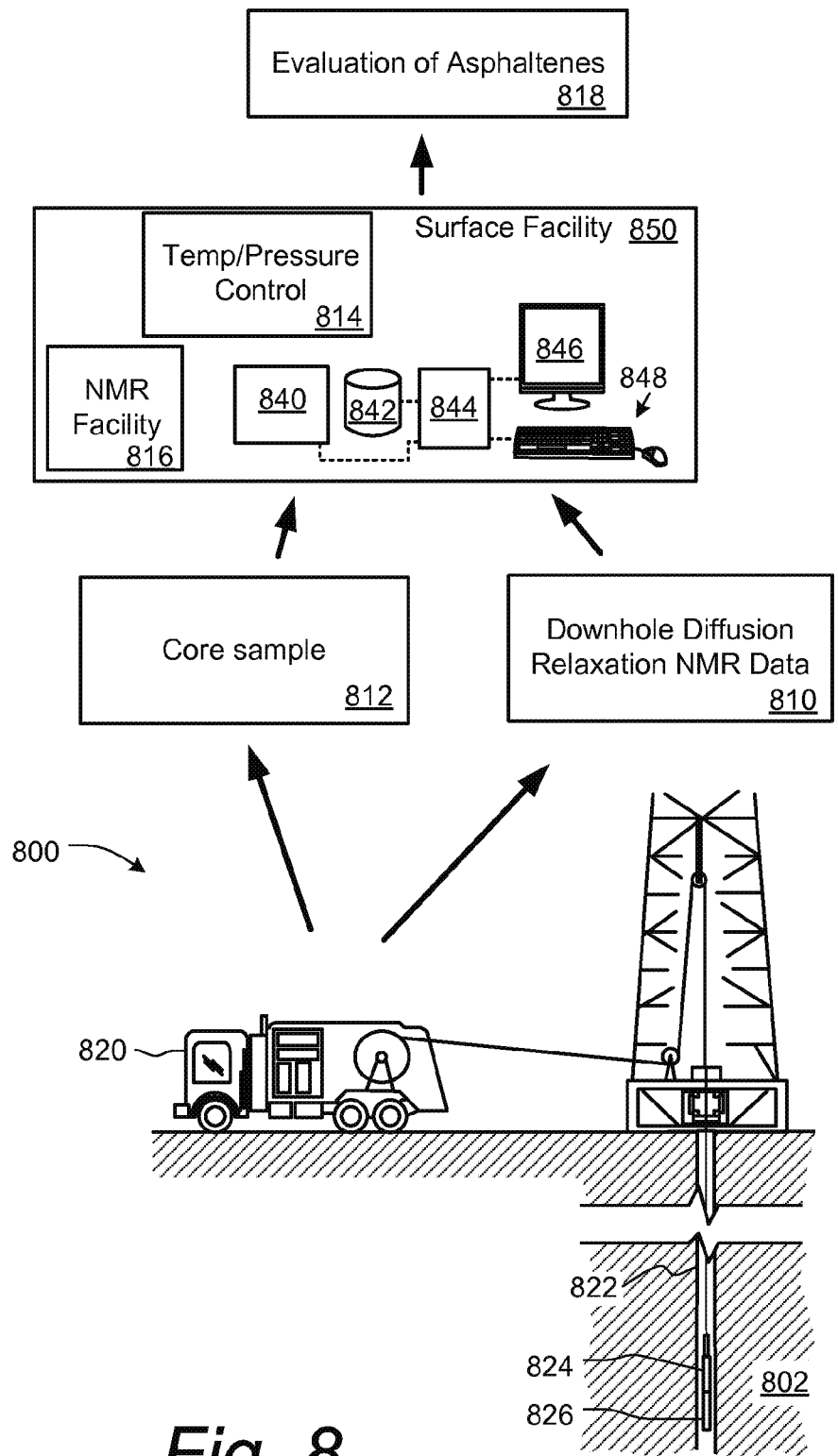
FIG. 8 is a diagram showing aspects of a system for evaluating whether or not significant amounts of asphaltenes are present in a core sample, according to some embodiments.

FIG. 8 is a diagram showing aspects of a system for evaluating whether or not significant amounts of asphaltenes are present in a core sample, according to some embodiments. NMR data from a subterranean rock formation 802 is being gathered at wellsite 800 via a Wireline truck 820 deploying a Wireline tool string in well 822. The tool string includes one or more Wireline tools such as tools 824 and 826. According to some embodiments, Wireline tool 824 is an NMR tool adapted to make NMR measurements downhole, including gathering $T_1$ and/or $T_2$ distribution data such as shown in block 710 of FIG. 7. According to some embodiments an NMR tool such as Schlumberger's CMR™ (Combinable Magnetic Resonance) tool is used, or Schlumberger's MR-Scanner™ (Magnetic Resonance Scanner) tool can be used for continuous Diffusion logging. According to some embodiments, Wireline tool 826 is a downhole tool adapted to take a core sample from the formation 802. Note that according to some embodiments, the NMR tool and core sampling tool are run at different times.

Acquired NMR data 810 is transmitted and the obtained core sample 812 is transported to the wellsite 800 to a surface facility 850 which includes one or more central processing units 844 for carrying out the data processing procedures as described herein, as well as other processing. Facility also includes a storage system 842, communications and input/output modules 840, a user display 846 and a user input system 848. According to some embodiments, the surface facility 850 may be located in a location remote from the wellsite 800. Surface facility 850 also includes a temperature/pressure control facility 814 for cycling the temperature as shown in blocks 714 and 716 of FIG. 7, as well as a NMR facility 816 that makes Diffusion—Relaxation measurements as shown in block 718 of FIG. 7. The processing units 844 are programmed to carry out the evaluation shown in block 720 of FIG. 7 so as to yield an evaluation of asphaltenes 818.

According to some alternate embodiments, the Wireline tools 824 and/or 826 are able to cut a core sample and cycle the temperature and/or pressure of the sample to below then back above the critical point for asphaltene drop out, and also to make NMR measurements before and after the cycling. According to further alternate embodiments, Wireline tools 824 and/or 826 are able to cool a sample portion of the rock formation 802 in-situ without cutting of a core, and NMR measurements are taken before and after temperature cycling to below and back above the critical point for asphaltene drop out. In such types of alternate embodiments, the data can either be transmitted to a surface facility or it can be evaluated downhole by the tools.

While the subject disclosure is described through the above embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the subject disclosure should not be viewed as limited except by the scope and spirit of the appended claims.

What is claimed is:

1. A method of asphaltene evaluation of a hydrocarbon-bearing rock sample from a subterranean rock formation comprising:
    making a first NMR measurement representative of the hydrocarbon-bearing rock sample at temperature and pressure conditions prior to asphaltene precipitation onset;
    lowering temperature and/or pressure of the hydrocarbon-bearing rock sample below an expected asphaltene precipitation onset condition;
    subsequently raising the temperature and/or pressure conditions above the expected asphaltene precipitation onset condition;
    making a second NMR measurement on the hydrocarbon-bearing rock while at conditions above the expected asphaltene precipitation onset condition; and
    evaluating asphaltene content of oil in the hydrocarbon-bearing rock sample based at least in part on a comparison of the first and second NMR measurements.

2. A method according to claim 1, wherein the first NMR measurement is made downhole using a downhole NMR tool while the rock sample is located in-situ within the subterranean rock formation.

3. A method according to claim 1, wherein the first NMR measurement is made on the surface on the rock sample while being preserved at reservoir temperature and pressure conditions.

4. A method according to claim 1, wherein temperature and pressure conditions of the rock sample for the first NMR measurement is substantially the same as temperature and pressure conditions of the rock sample for the second NMR measurement.

5. A method according to claim 1, wherein the first and second NMR measurements are diffusion-relaxation NMR measurements.

6. A method according to claim 5, wherein the first and second NMR measurements are diffusion-$T_2$ measurements.

7. A method according to claim 6, further comprising:
    mapping the first and second measurements in Diffusion and $T_2$ space; and
    evaluating the mapped first and second measurements for a shift in a fluid representing maltene tending to indicate significant presence of asphaltenes in the rock sample.

8. A method according to claim 7, wherein the shift indicates an irreversible behavior of asphaltenes on wettability of pore surfaces within the rock sample.

9. A method according to claim 1, wherein the first NMR measurement represents the rock sample at temperature and pressure conditions prior to production from the subterranean formation.

10. A method according to claim 1, wherein the expected asphaltene precipitation onset condition is a critical point for asphaltene flocculation-dissolution on an asphaltene-precipitation envelope.

11. A method according to claim 1, further comprising separating a signal representing a water fluid from a signal representing an oil fluid in data from the first and second NMR measurements.

12. A method according to claim 11, wherein the separating relies on a diffusion-coefficient log-mean of the data from the first and second NMR measurements.

13. A method according to claim 11, wherein the signal separation is performed at least partially manually.

14. A method according to claim 1, wherein the evaluation is further based in part on a calibration performed using laboratory analysis of saturates, aromatics, resins and asphaltenes conducted on oil extracted from and NMR measurements on one or more other samples of rock.

15. A system for asphaltene evaluation of a hydrocarbon-bearing rock sample from a subterranean rock formation comprising:
    a downhole NMR tool adapted to make a first NMR measurement of the subterranean rock formation at pressure conditions prior to asphaltene precipitation onset;
    a facility for controlling temperature and pressure of a hydrocarbon-bearing rock sample, the facility being configured to lower the temperature and/or pressure of the sample to a point below an expected asphaltene precipitation onset condition, and subsequently raise the temperature and/or pressure conditions above the expected asphaltene precipitation onset condition; and
    a surface NMR measurement facility adapted to make a second NMR measurement on the hydrocarbon-bearing rock sample while at conditions above the expected asphaltene precipitation onset condition, wherein an evaluation of asphaltene content in the hydrocarbon-bearing rock sample can be made based at least in part on a comparison of the first and second NMR measurements.

16. A system according to claim 15, wherein temperature and pressure conditions of the rock sample for the first NMR measurement is substantially the same as temperature and pressure conditions of the rock sample for the second NMR measurement.

17. A system according to claim 15, wherein the first and second NMR measurements are Diffusion-relaxation NMR measurements.

18. A system according to claim 17, wherein the first and second NMR measurements are Diffusion-$T_2$ measurements.

19. A system according to claim 18, further comprising a processing system configured and programmed to carry out the evaluation of asphaltene content based in part on a mapping of the first and second measurements in diffusion and T2 space, and evaluating the mapped first and second measurements for a shift in a fluid representing maltene tending to indicate significant presence of asphaltenes in the rock sample.

20. A system according to claim 19, wherein the shift indicates an irreversible behavior of asphaltenes on wettability of pore surfaces within the rock sample.

21. A system according to claim 15, wherein the first NMR measurement represents the rock sample at temperature and pressure conditions prior to production from the subterranean formation.

22. A system according to claim 15, wherein the expected asphaltene precipitation onset condition is a critical point for asphaltene flocculation-dissolution on an asphaltene-precipitation envelope.

23. A system according to claim 15, wherein the evaluating is further based in part on a calibration performed using laboratory analysis of saturates, aromatics, resins and asphaltenes conducted on oil extracted from and NMR measurements on one or more other samples of rock.

* * * * *